United States Patent [19]

Yamasawa

[11] Patent Number: 4,844,084

[45] Date of Patent: Jul. 4, 1989

[54] ELECTRONIC BLOOD PRESSURE METER

[75] Inventor: Tsutomu Yamasawa, Takatsuki, Japan

[73] Assignees: Omron Tateisi Electronics Co.; Isao Kai, both of Japan

[21] Appl. No.: 203,346

[22] Filed: Jun. 7, 1988

[30] Foreign Application Priority Data

Jun. 8, 1987 [JP] Japan ................. 62-142744

[51] Int. Cl.$^4$ .............................................. A61B 5/02
[52] U.S. Cl. ...................... 128/681; 128/686; 128/667
[58] Field of Search .................... 128/677–681, 128/686, 665–667, 687–690

[56] References Cited

U.S. PATENT DOCUMENTS

| 3,908,636 | 9/1975 | Page | 128/666 |
|---|---|---|---|
| 4,013,067 | 3/1977 | Kresse et al. | 128/666 |
| 4,129,124 | 12/1978 | Thalmann | 128/666 |
| 4,163,447 | 8/1979 | Orr | 128/666 |
| 4,331,155 | 5/1982 | Sacks | 128/686 |
| 4,406,289 | 9/1983 | Wesseling et al. | 128/679 X |

OTHER PUBLICATIONS

Hammer, W. E. et al., "Indirect Blood Pressure Measurement Cuff", IBM Tech Disclosure Bulletin, vol. 8, No. 4, Sep. 1965, p. 593.

Primary Examiner—Francis Jaworski
Attorney, Agent, or Firm—Wegner & Bretschneider

[57] ABSTRACT

In an electronic blood pressure meter for measuring blood pressure from a finger, there is provided a photoelectric sensor for detecting presence of a finger in the cuff. Thereby, it is made possible to positively avoid inflating the cuff without placing a finger therein and to prevent rupture and other damages to the cuff. In particular, since either a light emitting element or a light receiving element of the photoelectric sensor for detecting a finger is common to that of a photoelectric pulse wave detecting device incorporated in the cuff, the structure of the cuff is simplified and the manufacturing cost is reduced.

5 Claims, 7 Drawing Sheets

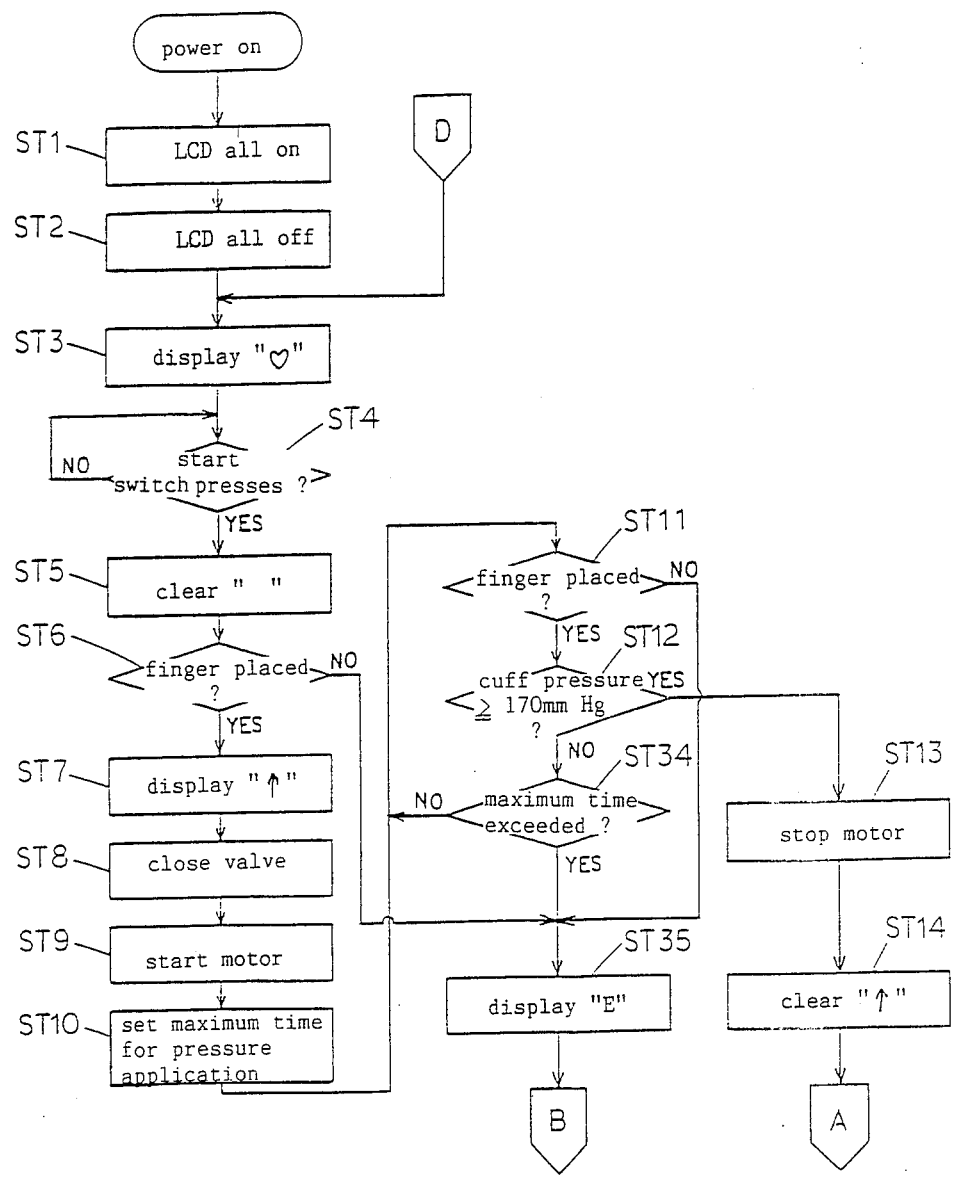

ELECTRONIC BLOOD PRESSURE METER

TECHNICAL FIELD

The present invention relates to an electronic blood pressure meter for measuring blood pressure values from a finger and in particular to such an electronic blood pressure meter having improved means for detecting presence of a finger in the cuff of the blood pressure meter.

BACKGROUND OF THE INVENTION

In an electronic blood pressure meter for detecting blood pressure values from a finger, the finger is, first of all, placed in a finger cuff for applying pressure to the finger, and blood pressure values are then computed from the change in the amplitude of pulse wave obtained from the finger as the cuff pressure is gradually reduced, according to a certain algorithm applied to a series of pulse wave data. In such an electronic blood pressure meter, since the finger cuff has inflatable air chambers which are limited in capacity as compared to an arm cuff which is more commonly used for measuring blood pressure, the cuff is less resistant against excessive pressurization particularly when the air chambers are inflated without placing a finger in the cuff. Further, if an excessive pressure is applied to the pressure sensor due to absence of a finger in the cuff, the pressure sensor may be damaged. Therefore, it is highly desirable not to inflate the cuff until a finger is placed in the cuff.

Conventionally, a micro switch was typically used for detecting presence of a finger in a finger cuff, but the micro switch occupies such a large space that the size of the finger cuff becomes larger than desired. And, some difficulty arises in assuring the reliability of the operation of the micro switch. An alternative possibility is to place a photoelectric sensor for detecting presence of a finger in the cuff, but the need for special component parts increases the complexity of the sensor and the manufacturing cost.

BRIEF SUMMARY OF THE INVENTION

In view of such problems of the prior art, a primary object of the present invention is to provide an electronic blood pressure meter for a finger having simple and economical means for detecting presence of a finger in the finger cuff.

A second object of the present invention is to provide an electronic blood pressure meter having reliable means for detecting presence of a finger in the finger cuff.

A third object of the present invention is to provide an electronic blood pressure meter having compact means for detecting presence of a finger in the finger cuff.

A fourth object of the present invention is to provide an electronic blood pressure meter having means for effectively preventing inadvertent inflation of a finger cuff without having a finger placed in the finger cuff.

These and other objects of the present invention can be accomplished by providing an electronic blood pressure meter for measuring blood pressure from a finger, comprising: a substantially cylindrical cuff for receiving a finger therein, provided with an inflatable air chamber; means for supplying pressurized air into the air chamber of the cuff; a pressure sensor for detecting a pressure of the cuff; pulse wave detecting means for detecting pulse wave from a finger placed in the cuff, comprising a light emitting element and a light receiving element; and blood pressure value determining means for determining a blood pressure value from outputs from the pulse wave detecting means and the pressure sensor; further comprising: a light emitting element for detecting presence of a finger in the cuff, attached to an inner circumferential surface of the cuff; a light receiving element for detecting presence of a finger in the cuff, attached to an inner circumferential surface of the cuff and adapted to receive light emitted from the light emitting element; and electronic circuit means for detecting presence of a finger in the cuff from an output of the light receiving element; the light emitting element of the pulse wave detecting means being common to the light emitting element for detecting presence of a finger in the cuff.

Presence of a finger in the cuff is accurately and reliably detected by the combination of a light emitting element and a light receiving element. Further, since a part of the pulse wave detecting means may be used as a part of the means for detecting presence of a finger in the cuff, the structure of the cuff is simplified and the advantages in reducing the manufacturing cost and the size of the cuff can be obtained at the same time.

According to a certain preferred embodiment of the present invention, the light emitting element and the light receiving element of the pulse wave detecting means are disposed adjacent to each other while the light receiving element for detecting presence of a finger in the cuff is disposed diagonally opposite to the light emitting element. Preferably, the light emitting element comprises a pair of light emitting devices such as LED's disposed on either side of the light receiving element of the pulse wave detecting means. Alternatively, the light receiving element of the pulse wave detecting means comprises a pair of light receiving sensors disposed on either side of the light emitting element of the pulse wave detecting means.

Thus, in either case, the reliability of both pulse wave detection and finger detection can be improved with the use of a minimum number of light emitting elements and light receiving elements. An advantage is obtained in terms of space if at least one of the light receiving elements and the light emitting elements is placed inside the air chamber.

BRIEF DESCRIPTION OF THE DRAWINGS

Now the present invention is described in the following with reference to the appended drawings, in which:

FIG. 1b is a sectional view of the finger cuff shown in FIG. 1a;

FIGS. 4a, 4b, 4c, and 4d are flow charts showing the operation of the electronic blood pressure meter shown in FIGS. 2 and 3.

DESCRIPTION OF THE PREFERRED EMBODIMENT

Figure 2:
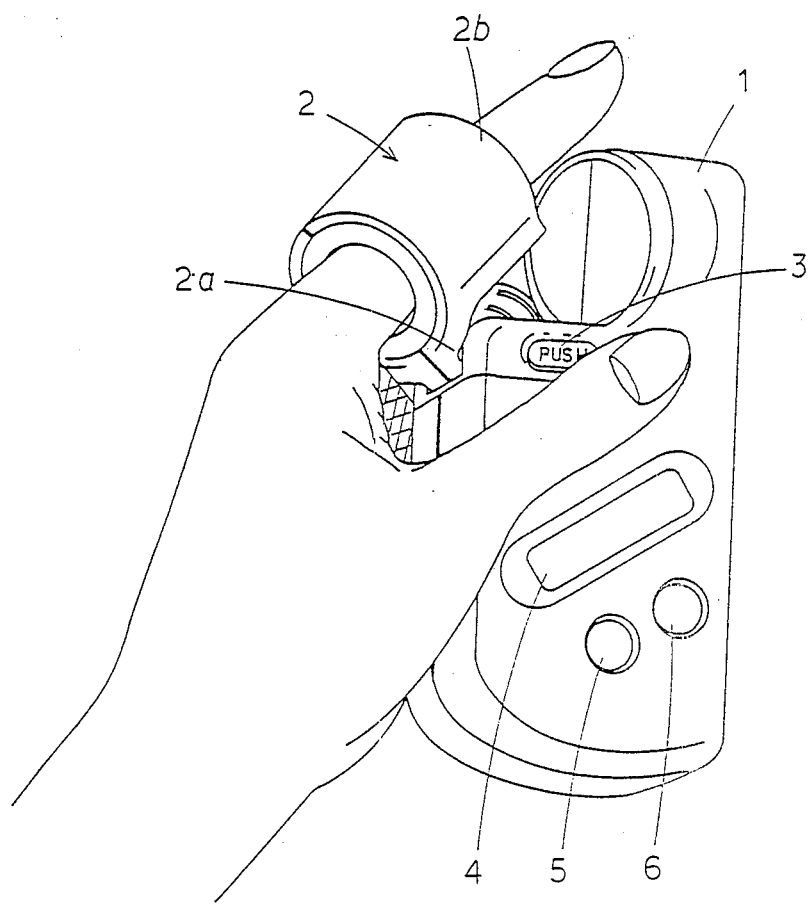
FIG. 2 is an overall perspective view of an electronic blood pressure meter for a finger showing how a finger is placed in the finger cuff of the present invention.

FIG. 2 is an external perspective view of an embodiment of the electronic blood pressure meter for a finger according to the present invention. This electronic blood pressure meter comprises a casing 1 having a finger cuff 2 pivotally attached thereto by way of a pivot mount 2a so that the finger cuff 2 may be rotated with respect to the casing 1 over a certain angle. The main part 2b of the finger cuff 2 may be pivoted away from the casing 1 when a push-button 3 is pressed so as to facilitate placing of a finger therein. The outer surface of the casing 1 is provided with a display unit 4, a power button switch 5 and a start button switch 6. The casing 1 is internally provided with an electronic circuit unit, a motor-driven pump and batteries as described hereinafter.

Figure 1A:
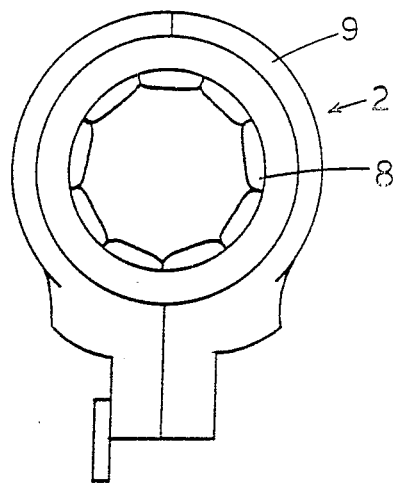
FIG. 1a is a front view of a finger cuff for electronically measuring blood pressure according to the present invention.
Figure 1B:
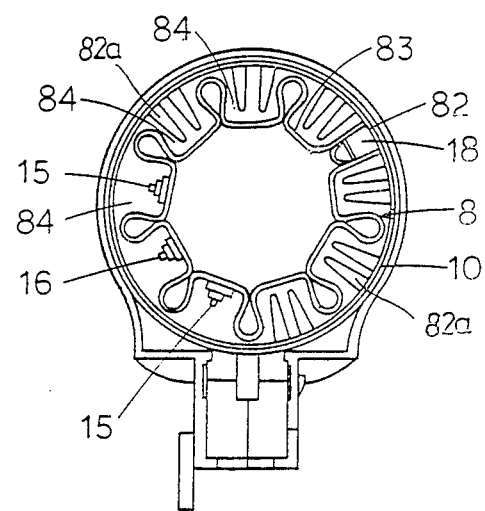

The finger cuff 2 comprises a cylindrical sleeve 10 and a cuff band 8 placed therein, and a cuff holder 9 comprising a pair of hollow semi-cylindrical clamps surrounding the sleeve 10 as shown in FIGS. 1a and 1b. The cuff band 8 comprises a strip of rubber base sheet 82, and a bag skin 83 bonded over the base sheet 82 so as to define a plurality air chambers 84 therebetween at equal interval along a circumferential direction. A light receiving element 16 is placed in one of the air chambers 84 while a pair of light emitting elements 15 are placed in the air chambers located on either side of the air chamber 84 accommodating the light receiving element 16 for the purpose of detecting pulse wave. These elements 15 and 16 are connected to the main circuit unit by way of lead wires not shown in the drawings. The air chambers 84 are communicated with the motor-driven pump in the casing 1 by way of a tube which is not shown in the drawings. Numeral 82a denote projections which are integrally formed with the base sheet 82 for guiding the finger substantially through a central part of the interior of the finger cuff 2.

Two light emitting elements 15 are used here instead of one so as to minimize any fluctuation in the results of pulse wave detection. An additional light receiving element 18 is placed in the inner circumferential surface of the sleeve 10 diagonally opposite to the other light receiving element 16 for the purpose of detecting an insertion of a finger into the finger cuff 2.

Here, it is possible to replace the light emitting elements 15 and the light receiving element 16 with light receiving elements and a light emitting element, respectively.

Figure 3:
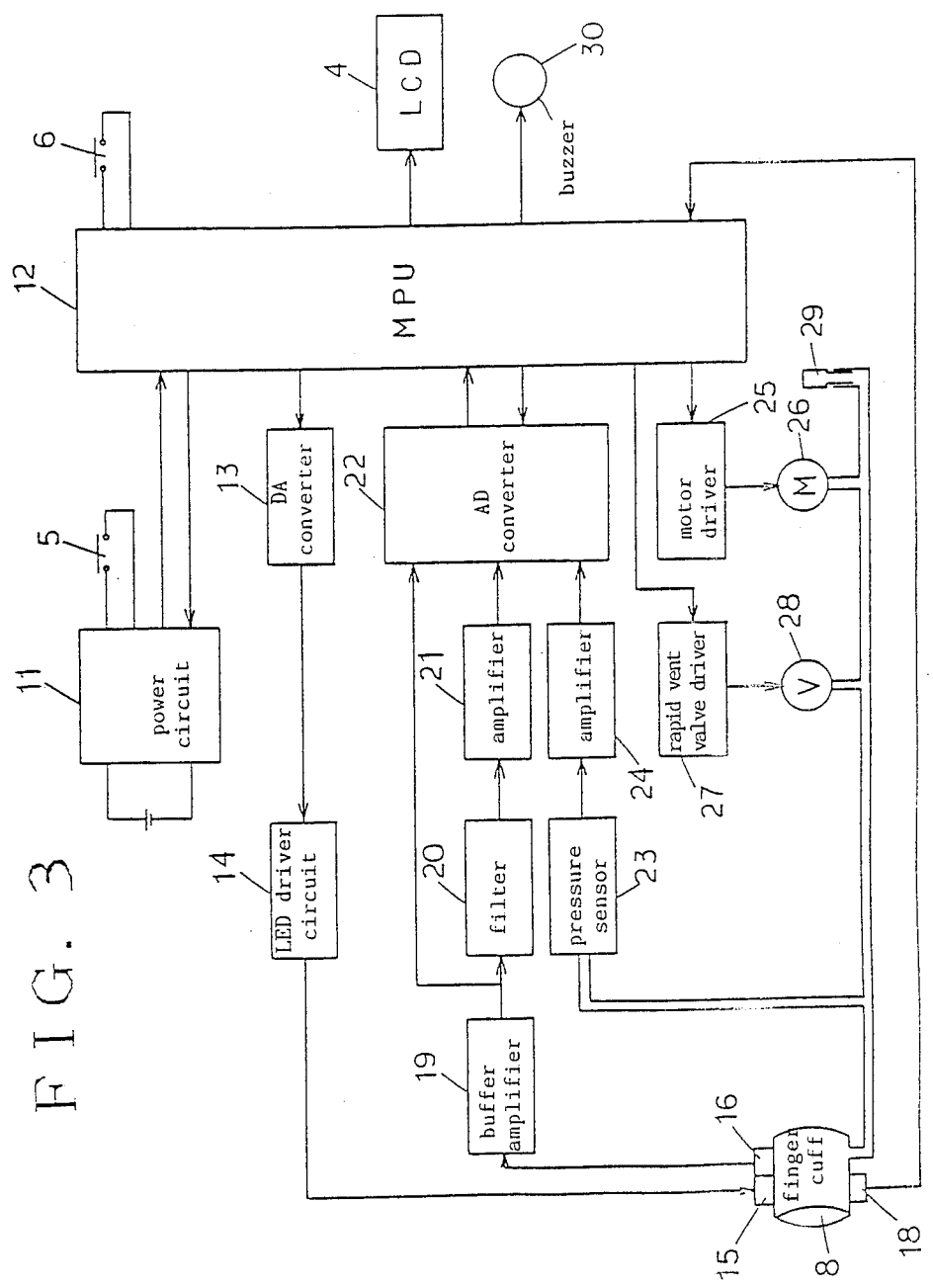
FIG. 3 is a circuit block diagram of the main circuit unit of the electronic blood pressure meter shown in FIG. 2.

FIG. 3 is a block diagram of the main circuit unit. When the power switch 5 is turned on, electric power is supplied to an MPU 12 and other parts of the circuit from a power source circuit 11. The MPU 12 activates a motor 26 by way of a motor driver circuit 25 to pressurize the finger cuff band 8 and vents the cuff band 8 by opening a valve 28 through a rapid vent valve driver circuit 27 to rapidly vent the pressurized air in the cuff band 8 as required. Pulse wave detection is carried out by the MPU 12 as the air chambers 84 are vented through a slow vent valve 29.

Further, a digital signal for determining the level of the brightness of the light emitting elements 15 is produced by the MPU 12, and the digital signal is converted into an analog signal by a DA converter 13. Output of the DC converter 13 is in turn supplied to an LED driver circuit 14 to illuminate the light emitting elements 15 at a selected brightness level. In this embodiment, the light emitting elements 15 can emit light in five different brightness levels according to the bit pattern of the digital control signal set up in the MPU 12. This is to compensate the differences in the amount of reflected light received by the light receiving element 16 from one subject person to another.

The pressure of the finger cuff 2 is detected by a semiconductor pressure sensor 23 and output from the pressure sensor 23 is supplied to the MPU 12 to be stored therein, by way of an amplifier 24 and an AD converter 22. Meanwhile, output from the light receiving element 16 is supplied to the MPU 12 by way of a buffer amplifier circuit 19, a filter circuit 20, an amplifier 21 and the AD converter 22, or directly from the buffer amplifier 19 through the AD converter 22. The direct path through the AD converter 22 from the light receiving element 16 and the buffer amplifier circuit 19 to the MPU 12 is provided for the purpose of obtaining the DC component of the output from the light receiving element 16. The MPU 12 adjusts the brightness level of the light emitting elements 15 according to this DC component. Output from the light receiving element 18 for detecting presence of a finger in the finger cuff 2 is also supplied to the MPU 12.

Basically, the MPU 12 generally performs the various signal processing functions to determine a systolic and a diastolic blood pressure value and displays these blood pressure values on the display unit 4. Further, to notify various states of the electronic blood pressure meter to the user, a buzzer 30 is activated by the MPU 12 as required.

Now the operation of the electronic blood pressure meter for a finger is described in the following with reference to the flow charts of FIGS. 4a through 4d.

When the power switch 5 is turned on, the MPU 12 lights up all the segments in the display unit 4 (ST1) and then turns off all the segments in the display unit 4 (ST2) to test the display unit 4. Then, a heart mark is displayed on the display unit 4 (ST3) to indicate the state of the readiness of the main circuit unit of the electronic blood pressure meter.

When the user presses the start switch 6 in this state, the determination result of ST4 becomes affirmative and the heart mark displayed on the display unit 4 is cleared (ST5). (The determination result of ST4 remains negative and the system stay in this step indefinitely until the start switch 6 is pressed.) It is then determined whether a finger has been placed in the finger cuff 2 or not (ST6). This determination process is carried out by determining whether the light directed to the light receiving element 18 has been interrupted or not. In other words, when the user has placed his finger into the finger cuff 2, the finger prevents the light from being emitted from the light emitting elements 15 and it is detected by the light receiving element 16 as an interruption of light. If a finger has indeed been placed in the cuff 2 as shown in FIG. 2, the determination result of ST6 becomes affirmative and an upward directed arrow is displayed on the display unit 4 (ST7). This arrow mark indicates the beginning of the action of pressurizing the cuff band 8 and the valve 28 is closed at the same time (ST8).

Subsequently, the motor driver circuit 25 is activated to drive the motor-driven pump (ST9). Then, the maximum time interval for pressure application is set up (ST10). After the pressurization of the cuff is started, it is determined again whether the finger is still placed in the finger cuff 2 or not (ST11). If the finger is still placed in the finger cuff 2, the process of pressurization is continued. It is then determined whether the cuff pressure has reached the level of 170 mmHg or not (ST21). If this level has not been reached, it is determined whether the maximum time interval has elapsed or not (ST34). If not, the system flow returns to ST11 and the process of pressurization is continued.

If this target level of pressure has been reached, the system flow advances from ST12 to ST13 and ST14, and the motor 26 is stopped and the upward arrow displayed on the display unit 4 is cleared. This concludes the process of pressurization.

On the other hand, presence of a finger is not detected in ST6 or ST11, it means that no finger is placed in the cuff and a state of error has occurred. Therefore, "E" is displayed on the display unit 35 and the system flow advances to ST36.

Following ST14, to detect pulse wave, the LED is lighted up at the brightness level of 3 (ST15). It is determined whether the DC component of the pulse wave detected by light receiving element 16 is higher than a certain prescribed value or not (ST16). If the DC component of the pulse wave is higher than the prescribed value, it means that the amplitude of the reflected light is insufficient and the brightness level is increased by one level or to level 4 (ST17). The brightness level is then evaluated again in ST18 and if the brightness level is still insufficient the brightness is further increased by one more level or to level 5 (ST19). In ST20, the brightness level is evaluated again. If the brightness is still insufficient, since there is not any higher brightness level, the system flow advances to ST36. If the brightness level is not insufficient in ST18 or ST20, it means that the brightness level is proper and level 4 or level 5, as the case may be, is maintained thereafter. In these cases, the system flow advances to ST26 in FIG. 4c.

In ST16 or in the state of level 3, if the pulse wave level is not too high, it is then determined whether the pulse wave level is too low or not in ST21. If the pulse wave is not too low, it means that the pulse wave level is in linear range and the level 3 brightness level is proper. Therefore, the system flow advances to ST26 in FIG. 4c.

On the other hand, if the pulse wave level is found to be too low in ST21, the LED brightness level is reduced to level 2 (ST22) and it is again determined whether the pulse wave level is too low or not in ST23. If it is too low, the system flow advances to ST24 and the LED brightness level is reduced to level 1 and it is again determined whether the LED brightness level is too low or not in ST25. If the brightness level is found to be proper at level 2 or level 1, the LED brightness level is maintained at that level and the system flow advances to ST26 in FIG. 4c.

Figure 4B:
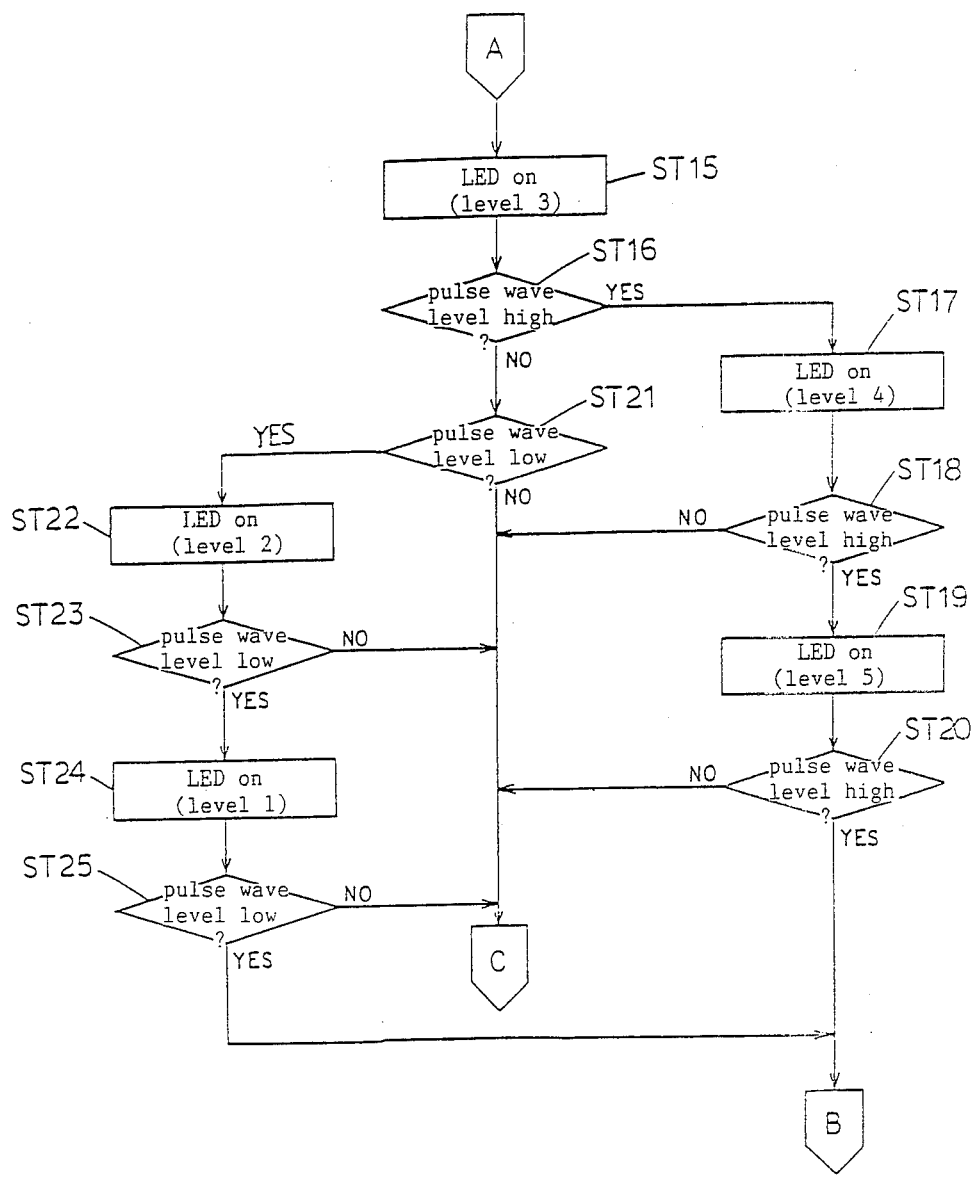
Figure 4C:
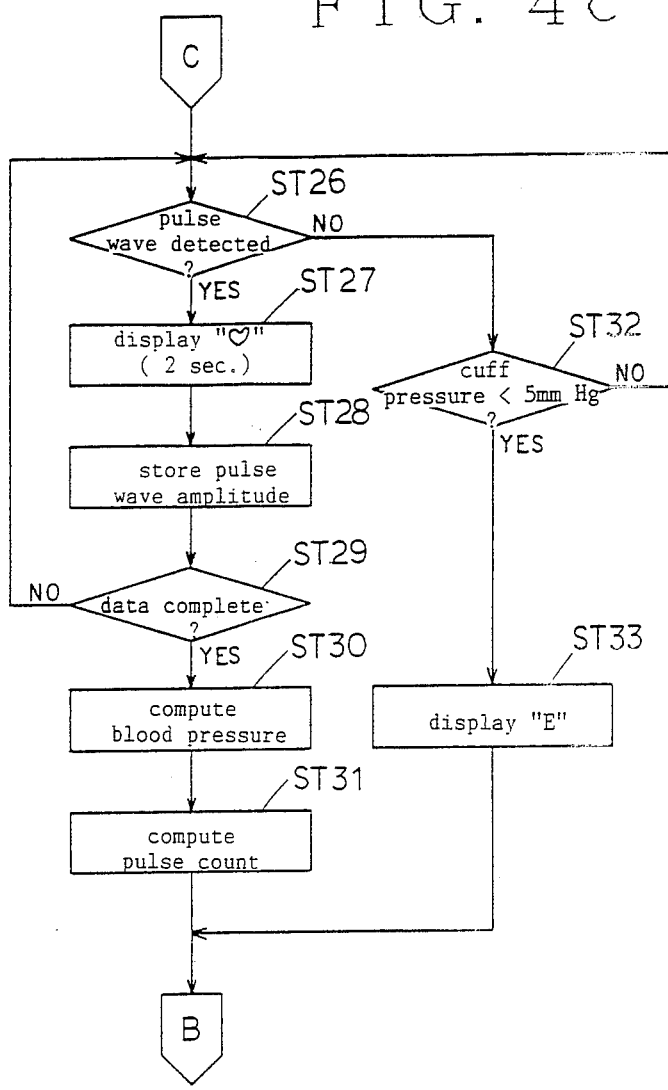
Figure 4D:
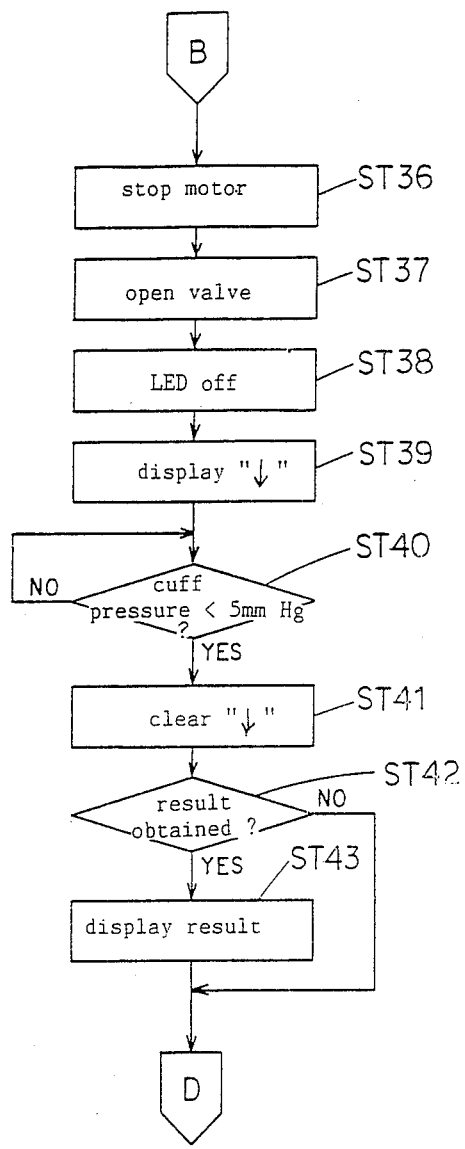

The steps from ST15 to ST25 shown in FIG. 4b are actually conducted by the MPU 12 as a process of adjusting the brightness level of the light emitting elements 15 to obtain an optimum pulse wave level while a finger is placed in the finger cuff 2. If the pulse wave level is found to be proper, the system flow advances to ST26 shown in FIG. 4c and it is determined whether pulse wave has been detected or not. If the pulse wave has not been detected in ST26, it is determined whether the cuff pressure is equal to or less that 20 mmHg or not in ST32. If no pulse wave has been detected even when the cuff pressure has dropped below 20 mmHg, it is understood as an abnormal state and an error display "E" is made on the display unit 4 in ST33. The system flow then advances to ST36.

If pulse wave is detected in ST26, the heart mark is displayed on the display unit 4 for 0.2 seconds in ST27 and the pulse wave amplitude at that instance is stored in ST28. At this stage, it is determined whether all the data required for computing blood pressure values according to a certain algorithm has been collected or not in ST29. If not, the system flow returns to ST26, and the pulse wave detection is continued until all the data for blood pressure value computation is obtained.

When it is found that all the data has been collected in ST29, blood pressure values are computed in ST30 and a pulse count is computed in ST31. Then, the system flow advances to ST36.

There are a number of algorithms for computing blood pressure values. For instance, the cuff pressure at which a pulse wave amplitude is obtained is determined as a systolic blood pressure and the cuff pressure corresponding to 70% of the maximum pulse wave amplitude is determined as a diastolic blood pressure.

Either when the measurement has been completed or when the measurement was found to be a failure, the motor 26 is stopped in ST36 and the valve 28 is opened to rapidly vent air from the air chambers 34 of the finger cuff 2, followed by clearing of the display on the display unit 4 (ST38) and displaying a downward arrow on the display unit 4 (ST39). The downward arrow represents a rapid venting of the cuff.

When the cuff pressure is found to be equal to or less than 5 mmHg in ST40, the downward arrow is cleared ST41 and it is determined whether a measurement result has been obtained or not in ST42. If a proper measurement result has been obtained, the result is displayed in ST43 and the system flow returns to ST3. If there is no measurement result or a state of error has been detected, the system flow returns to ST3 without any displaying process and the system is made ready for the next measurement process.

Thus, according to the present invention, since the placement of a finger is detected by a combination of a light emitting element and a light receiving element, no specialized sensor for detecting the presence of a finger is required. Further, the finger cuff may be made smaller and more economical to manufacture. In particular, since a part of the finger detector is shared by a sensor for detecting pulse wave, the above mentioned advantages are even more enhanced.

Although the present invention has been shown and described with reference to the preferred embodiment thereof, it should not be considered as limited thereby. Various possible modifications and alterations could be conceived of by one skilled in the art to any particular part of the invention without departing from the scope of the invention.

What I claim is:

1. An electronic blood pressure meter for measuring blood pressure from a finger, comprising:
a substantially cylindrical cuff for receiving a finger therein, provided with an inflatable air chamber;
means for supplying pressurized air into the air chamber of the cuff;
a pressure sensor for detecting a pressure of the cuff;
pulse wave detecting means for detecting pulse wave from a finger placed in the cuff, comprising a light emitting element and a light receiving element; and
blood pressure value determining means for determining a blood pressure value from outputs from the pulse wave detecting means and the pressure sensor;

further comprising:

a light emitting element for detecting presence of a finger in the cuff, attached to an inner circumferential surface of the cuff;

a light receiving element for detecting presence of a finger in the cuff, attached to an inner circumferential surface of the cuff and adapted to receive light emitted from the light emitting element; and electronic circuit means for detecting presence of a finger in the cuff from an output of the light receiving element;

the light emitting element of the pulse wave detecting means being common to the light emitting element for detecting presence of a finger in the cuff.

2. An electronic blood pressure meter for a finger as defined in claim 1, wherein the light emitting element and the light receiving element of the pulse wave detecting means are disposed adjacent to each other while the light receiving element for detecting presence of a finger in the cuff is disposed diagonally opposite to the light emitting element.

3. An electronic blood pressure meter for a finger as defined in claim 2, wherein the light emitting element of the pulse wave detecting means comprises a pair of light emitting devices disposed on either side of the light receiving element of the pulse wave detecting means.

4. An electronic blood pressure meter for a finger as defined in claim 2, wherein the light receiving element of the pulse wave detecting means comprises a pair of light sensors disposed on either side of the light emitting element of the pulse wave detecting means.

5. An electronic blood pressure meter for a finger as defined in claim 1, wherein at least one of the light receiving elements and the light emitting element is placed inside the air chamber.

* * * * *